United States Patent [19]
Fischer et al.

[11] Patent Number: 6,162,101
[45] Date of Patent: Dec. 19, 2000

[54] CONNECTOR ASSEMBLY FOR ELECTRODES

[75] Inventors: Reid M. Fischer, Minneapolis; Alfred A. Iversen, Wayzata, both of Minn.

[73] Assignee: PMT Corporation, Chanhassen, Minn.

[21] Appl. No.: 09/146,589

[22] Filed: Sep. 3, 1998

[51] Int. Cl.[7] ................................................ H01R 4/48
[52] U.S. Cl. .................. 439/729; 439/819; 439/835; 439/909; 128/642
[58] Field of Search ................................. 439/725, 729, 439/909, 656, 835, 817, 819

[56] References Cited

U.S. PATENT DOCUMENTS

| | | |
|---|---|---|
| 3,989,345 | 11/1976 | DeVito ................................. 339/254 |
| 4,850,359 | 7/1989 | Putz . |
| 4,869,255 | 9/1989 | Putz . |
| 5,354,326 | 10/1994 | Comben et al. . |
| 5,560,358 | 10/1996 | Arnold et al. . |
| 5,782,892 | 7/1998 | Castle et al. ............................... 607/37 |

*Primary Examiner*—Paula Bradley
*Assistant Examiner*—Truc Nguyen
*Attorney, Agent, or Firm*—Anthony G. Eggink

[57] ABSTRACT

A connector assembly and method for electrically connecting an implantable electrode having an electrical lead array to monitoring equipment. The connector assembly includes a lead holder, an electrical conductor array, and a base holding the electrical conductor array, and a resilient element. The lead holder is moveable with respect to the base from a first position to an operating position. The resilient element is adapted to bias the lead holder from the first position to the operating position.

20 Claims, 4 Drawing Sheets

CONNECTOR ASSEMBLY FOR ELECTRODES

FIELD OF THE INVENTION

This invention is related to connector devices for medical electrodes. More particularly, this invention is related to connector devices which permit the transfer of electrical signals from a surgically implanted electrode to an external monitoring device, such as an electroencephalograph.

BACKGROUND OF THE INVENTION

The use of implantable electrodes to measure the electrical activity of the brain has been known for many years. These electrodes may have various shapes but commonly have multiple contacts to record activity at several locations simultaneously. This is particularly useful when determining the areas of the brain involved in an epileptic seizure, for example.

The electrodes require a connection to an external monitor. To monitor brain activity, the electrodes must ultimately be connected to an electroencephalograph. The electrode typically has a lead cable which carries the lead wires from the contacts in the electrode to a terminal or lead array. Typically, it is preferable that this lead cable be of sufficiently narrow diameter to be inserted under a patient's skin for a desired distance. This lead array is not compatible to be linked directly to a monitoring apparatus. Thus a connector device or assembly having electrical contacts compatible with the external monitoring apparatus is needed.

Prior art designs for connector assemblies include those having two or more separable pieces which must be assembled to bring the lead cable in contact with other electrical contacts or conductors, thus forming the electrical connection leading to the external monitoring device. Other designs include actuator means which must be moved or turned in order to bring the lead cable in contact with the electrical conductors.

An unmet need in this art is a connector assembly that combines ease of use with reliability of operation.

SUMMARY OF THE INVENTION

This invention is a connector assembly for electrically connecting an implantable electrode having an electrical lead array to monitoring equipment, comprising a lead holder, an electrical conductor array, and a base holding the electrical conductor array, such that the lead holder is moveable with respect to the base from a first position to an operating position, and a resilient element adapted to bias the lead holder from the first position to the operating position.

Preferably, the resilient element biases the lead holder toward the base. In another embodiment, the resilient element biases the base toward the lead holder. The resilient element may be a leaf spring, a coil spring, a piston, or a plunger.

In one embodiment, the holder has a channel through which the lead array is inserted, and the base holding the electrical conductor array has an opening adapted to be aligned with the channel in the holder. The resilient element is mounted on the base and causes the electrical connector array to be biased against the lead array, and the holder moves relative to the base such that when the opening in the base is aligned with the channel in the holder, the lead array is inserted into the channel thus causing electrical contact between the lead array and the electrical conductor array.

In another embodiment, this invention is a connector assembly for electrically connecting an implantable electrode having an electrical lead array to monitoring equipment, comprising a lead holder, an electrical conductor array, a base holding the electrical conductor array, wherein the lead holder is moveable with respect to the base from a first position to an operating position, and a means of biasing the lead holder from the first position to the operating position.

In another aspect, this invention is a method for electrically connecting a lead array from an electrode to an external monitoring device, comprising providing a connector assembly as described above, inserting the lead array into the lead holder, and urging the lead array and the base toward each other by means of the resilient element, thus making electrical contact between the lead array and the electrical conductor array.

BRIEF DESCRIPTION OF THE DRAWINGS

Aspects of the present invention will be understood with reference to the detailed description of specific embodiments of the invention, which follows, when read in conjunction with the accompanying drawings, wherein.

DETAILED DESCRIPTION OF THE PREFERRED EMBODIMENTS

This invention is a connector assembly and a method of using this assembly to electrically connect a lead array from an electrode to an external monitoring device by making contact between the lead array and an electrical conductor array. The lead holder and the base are moveable with respect to each other from a first position, without the lead array, to an operating position in which the lead array makes contact with the electrical conductor array.

The lead array has at least one lead and typically has five or more leads. The connector assembly is constructed from separate elements and assembled as a one-piece unit and can conveniently and advantageously be held in one hand while the lead array is either inserted into it or removed from it. Preferably, the connector assembly is provided with a transparent view window, which permits the health care worker to observe the alignment of the lead array with the electrical conductor array to assure proper contact and to verify the absence of any foreign objects that would interfere with the proper functioning of the connector. The connector assembly typically is fabricated from plastic materials, though any material that can be molded or machined is suitable for use.

Figure 1:
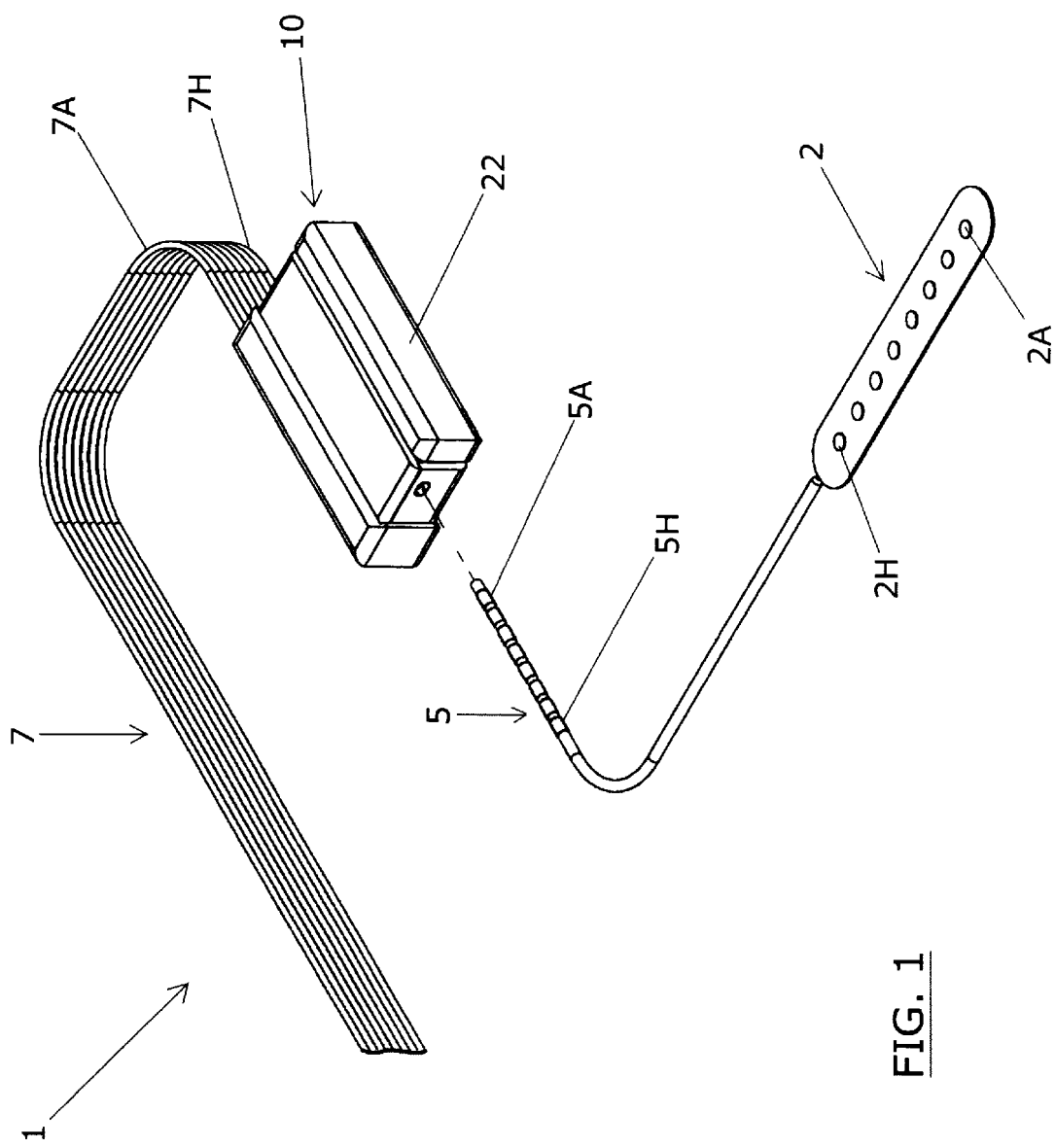
FIG. 1 is a perspective view of one embodiment of the connector assembly of this invention.

Electrode system 1 is shown in FIG. 1 and comprises lead array 5 which is formed from the leads of implantable multiple contact electrode 2. Though eight contacts (2A through 2H) are shown for this electrode, as few as one and as many as 32 (in conjunction with a single lead array) could be used. Electrode 2 typically is a strip or grid of contacts held in place between two layers of biocompatible silicone. Contacts 2A through 2H are electrically connected by leads to respective contacts 5A through 5H at the end of a tail that forms lead array 5. The leads are insulated from one another and from body tissue by coating them with a suitable insulating material such as biocompatible silicone. The contacts of the implantable electrode are shown in a linear array, but other configurations could be used. In similar fashion, the lead array at the tail of the electrode does not have to be a linear array, as the connectors could be adapted to accept other lead arrangements (such as a grid or a circle), as known to one of skill in the art. Lead array 5 fits into connector assembly 10. Cable 7 comprises individual connection wires 7A through 7H and forms the electrical connection from assembly 10 to an external monitor (not shown).

Figure 2A:
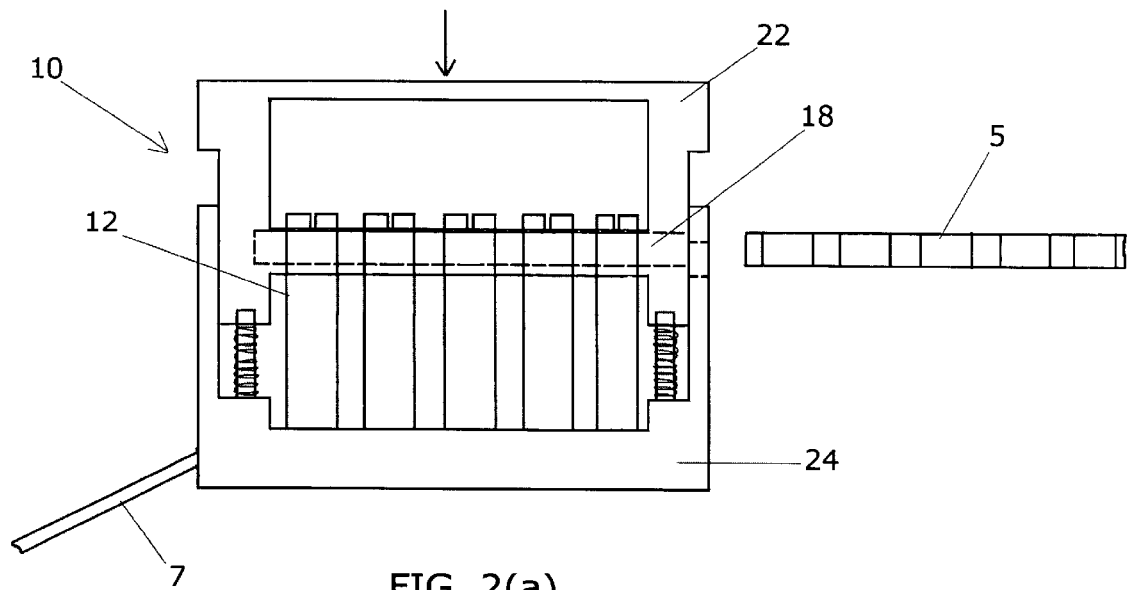
FIGS. 2(*a*) and 2(*b*) are diagrammatic views illustrating insertion of the lead array into the connector assembly.
Figure 2B:
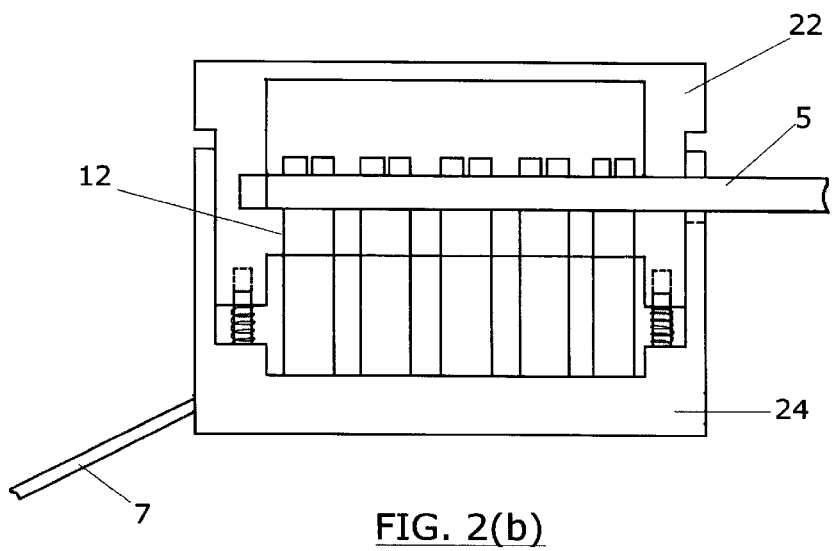

FIGS. 2(a) and 2(b) illustrate the insertion of lead array 5 into connector assembly 10. For the sake of illustration, the dimensions of the connector assembly are not to scale and only five lead contacts are shown. FIG. 2(a) illustrates a rest position of the lead holder relative to the base. Lead holder cap 22 is pushed down, thus moving the lead holder to an insertion position which aligns channel 18 of the lead holder with hole 15 in base 14 and allows lead array 5 to be inserted into channel 18. When lead holder cap 22 is released, resilient element 20 biases the lead array holder against the contacts of the electrical contact array thus forming the operating position of the connector assembly.

Figure 3:
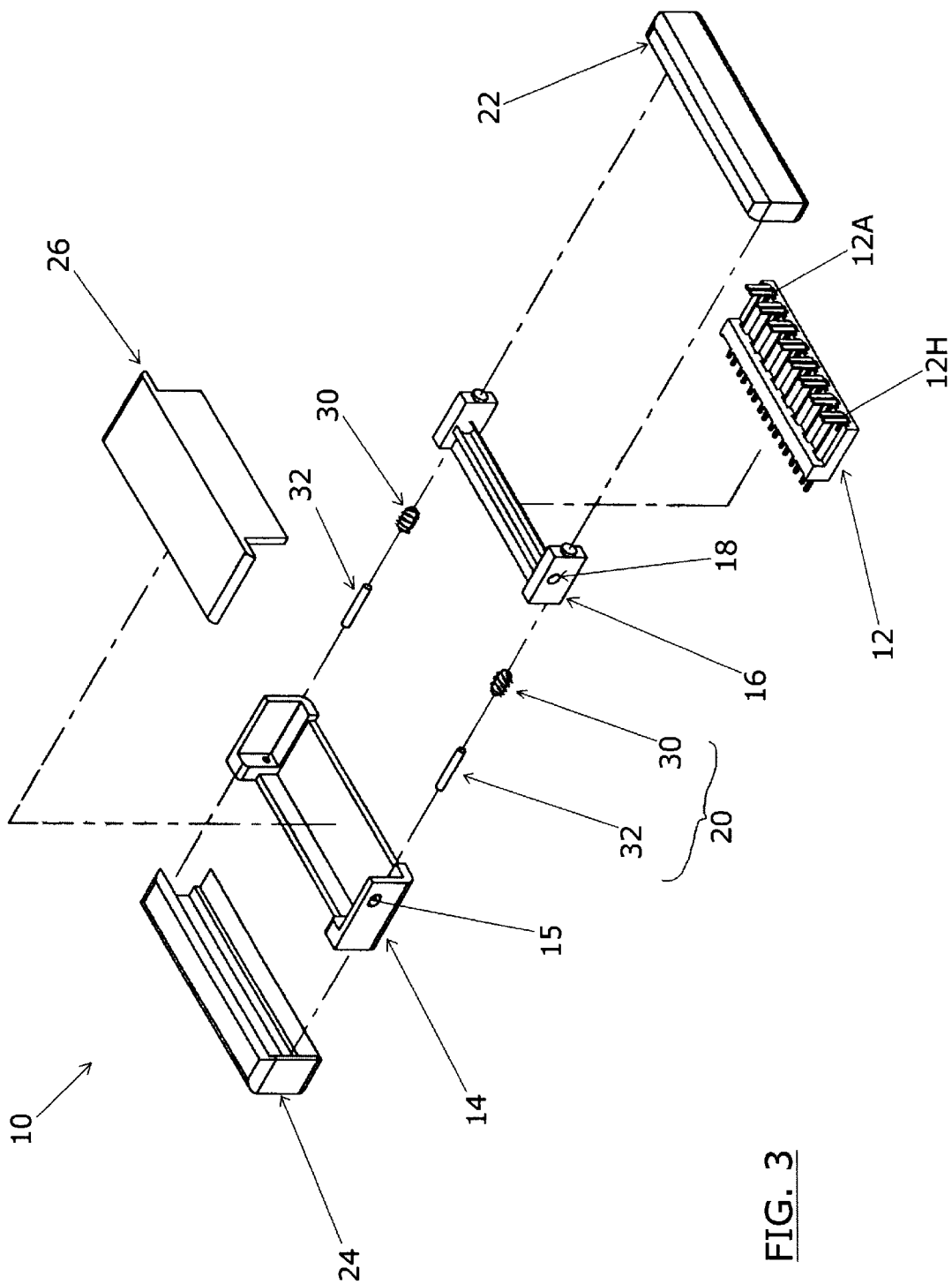
FIG. 3 is a exploded view of one embodiment of this invention.
Figures 5A, 5B:
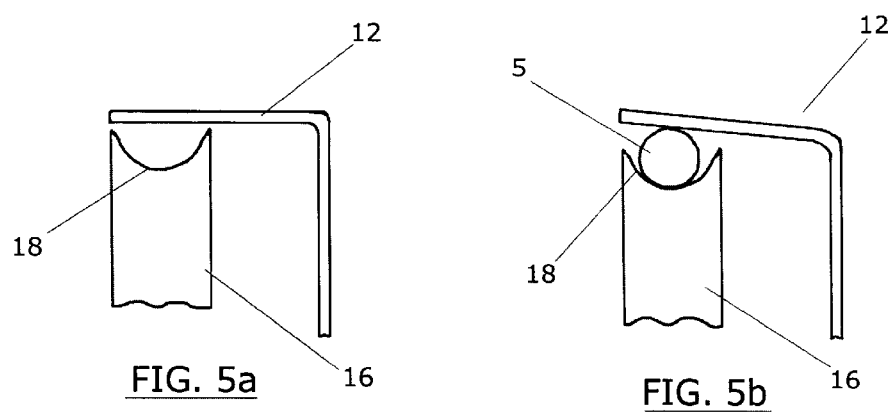
FIGS. 5(*a*) and 5(*b*) are cross-sectional views illustrating contact of the lead array with the conductor array.

FIG. 3 shows an exploded view of a preferred embodiment of connector assembly 10. Electrical conductor array 12, comprises conductors 12A through 12H and is held in position by base 14. The individual members of array 12 are configured as shown in FIG. 5(a) and (b) and thus face lead holder 16. Lead holder 16 having open channel 18 therethrough is held in a rest position by resilient element 20. An insertion position to allow for insertion of the lead array is achieved by movement of lead holder 16 toward base 14 causing hole 15 in base 14 to align with channel 18. The lead array is biased against electrical conductor array 12 by the action of resilient element 20. Base 14 also has opening 15, shown in the Figure as a hole, which aligns with channel 18 in lead holder 16. Opening 15 may be a hole, a slot, or an open side, but preferably is a hole which aids in the alignment of the base and the lead holder during insertion of the lead array. Channel 18 is open in the area that faces the electrical conductor contacts. Lead array 5 is held within channel 18 in proper alignment such that contacts 5A through 5H make electrical connection with conductors 12A through 12H, respectively, as shown in a cross-sectional view in FIGS. 5(a) and 5(b). Resilient element 20 is shown in FIG. 2 as coil springs 30 fitting over support rods 32 which are fitted into base 14 on either side of conductor array 12. The resilient element causes the lead array to push against the electrical connectors, thus making electrical contact. Typically the electrical connectors bend slightly due to the force of the lead array against them as best seen in FIGS. 5(a) and 5(b). Lead holder cap 22 fits over and typically is adhered to the lead holder. Cover 26, which is preferably transparent, fits over base 14 and lead holder 16 and between lead holder 16 and lead holder cap 22 and also serves to protect electrical conductor array 12. Base cap 24 is fitted onto and is typically adhered to the base and provides a passageway through which passes cable 7 (as shown in FIG. 1). Individual conductors 12A through 12H making up conductor array 12 are connected (respectively) to wires 7A through 7H (not shown in FIG. 2) forming cable 7 which feeds through and is protected from damage or abrasion by base cap 24.

As further shown in FIG. 3, the conductors 12A–H of the conductor array 12 have a slit in the upwardly extending end of each conductor element to provide a bifurcated structure to better contour the conductor ends for electrical engagement with contacts 2A–2H of the array 5.

Figure 4:
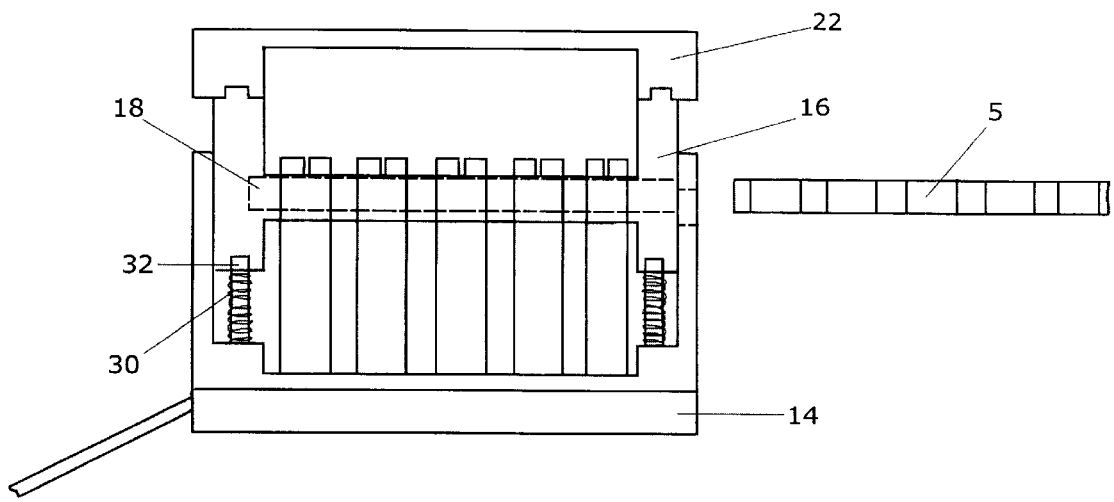
FIG. 4 is a cross-sectional view of the connector assembly of one embodiment of this invention.

FIG. 4 shows a cross-section of a portion of connector assembly 10. Resilient element 20 comprises coil springs 30 mounted on support rods 32 which are themselves mounted on electrical conductor base 14 such that the electrical conductor array (not shown) fits between the support rods Lead holder 16 is slidably disposed over the support rods. Alternatively, the resilient element may comprise a leaf spring, a piston, a plunger, resilient material or like elements which are capable of providing an opposing force to the lead holder. Regardless of the type of resilient element, lead holder cap 22 is moved from a rest position, to an insertion position, which permits the insertion of lead array 5 through channel 18. In the third, or operating position of the connector assembly, the force on lead holder cap 22 has been released, causing electrical contact to be made between the lead array and the electrical conductor array by action of the resilient element biasing the lead array holder toward the connector array. The alignment of lead array 5 with the contacts of the electrical conductor can then be verified by viewing through the transparent cover (i.e., 26 in FIG. 3).

FIGS. 5(a) and 5(b) illustrate in cross-section the lead array holder in a first position, without the lead array (i.e., either the rest position or the insertion position) to the operating position (with the lead array inserted in channel 18 and making electrical contact). The resilient element biases the lead array holder toward a connector from the connector array, thus making electrical contact between the lead array and the connector array. Channel 18 holds the lead array in proper alignment. The electrical conductors in the connector array (12A through 12H) preferably are sufficiently flexible so that they bend or yield somewhat when the lead array is pressed against it. This ensures that all leads make good electrical contact.

Although a particular embodiment of the invention has been disclosed herein in detail, this has been done for the purposes of illustration only, and is not intended to be limiting with respect to the scope of the appended claims. It is contemplated that various substitutions, alterations, and modifications may be made to the embodiment of the invention described herein without departing from the spirit and scope of the invention as defined by the claims.

What is claimed is:

1. A connector assembly having an interior for electrically connecting an implantable electrode having an electrical lead array to monitoring equipment, comprising:

a nonconducting lead holder, an electrical conductor array positioned in the interior of said connector assembly, a nonconducting base holding the electrical conductor array, wherein the lead holder is moveable with respect to the base from a first position to an operating position, and a resilient element adapted to bias the lead holder from the first position to the operating position.

2. A connector assembly as in claim 1 wherein the resilient element is selected from a leaf spring, a coil spring, a piston, or a plunger.

3. A connector assembly as in claim 1 wherein the lead holder comprises a channel through which the lead array is inserted.

4. A connector assembly as in claim 1 wherein the resilient element is adapted to bias the lead holder in the direction of the conductor array.

5. A connector assembly as in claim 1 wherein the resilient element is adapted to bias the conductor array in the direction of the lead holder.

6. A connector assembly having an interior for electrically connecting an implantable electrode having an electrical lead array to monitoring equipment, comprising:
- a nonconducting lead holder having a channel through which the lead array is inserted,
- an electrical conductor array in the interior of said connector assembly,
- a nonconducting base holding the electrical conductor array, having an opening adapted to be aligned with the channel in the holder and having thereon a resilient element which causes the electrical connector array to be biased against the lead array, wherein the holder moves relative to the base such that when the opening in the base is aligned with the channel in the holder, the lead array is inserted into the channel causing electrical contact between the lead array and the electrical conductor array.

7. A connector assembly as in claim 6 wherein the resilient element is selected from a leaf spring, a coil spring, a piston, or a plunger.

8. A connector assembly having an interior for electrically connecting an implantable electrode having an electrical lead array to monitoring equipment, comprising:
- a nonconducting lead holder,
- an electrical conductor array positioned in the interior of said connector assembly,
- a nonconducting base holding the electrical conductor array,
- wherein the lead holder is moveable with respect to the base from a first position to an operating position, and
- a means of biasing the lead holder from the first position to the operating position.

9. A connector assembly as in claim 8 wherein the means of biasing is selected from a leaf spring, a coil spring, a piston, or a plunger.

10. A connector assembly as in claim 8 wherein the means of biasing the lead holder is adapted to bias the lead holder in the direction of the conductor array.

11. A connector assembly as in claim 8 wherein the means of biasing the lead holder is adapted to bias the conductor array in the direction of the lead holder.

12. A method for electrically connecting a lead array from an electrode to an external monitoring device, comprising:
providing a connector assembly having an interior and comprising:
- a nonconducting lead holder,
- an electrical conductor array positioned in the interior of the connector assembly,
- a nonconducting base holding the electrical conductor array, wherein the lead holder is moveable with respect to the base from a first position to an operating position, and
- a resilient element adapted to bias the lead holder from the first position to the operating position;
inserting the lead array into the lead holder, and
urging the lead array and the base toward each other by means of the resilient element, thus making electrical contact between the lead array and the electrical conductor array.

13. The method of claim 12 wherein in the step of providing the connector assembly, the resilient element is selected from a leaf spring, a coil spring, a piston, or a plunger.

14. The method of claim 12 wherein in the step of providing the connector assembly, the lead holder comprises a channel through which the lead array is inserted.

15. The method of claim 12 wherein in the step of providing the connector assembly, the resilient element is adapted to bias the lead holder in the direction of the conductor array.

16. The method of claim 12 wherein in the step of providing the connector assembly, the resilient element is adapted to bias the conductor array in the direction of the lead holder.

17. The connector assembly of claim 8 wherein said assembly includes a transparent cover.

18. The connector assembly of claim 1 wherein said connector assembly further comprises a base, a base cap, a cover and a lead holder cap and wherein said cover is transparent to allow viewing the interior of said connector assembly.

19. The connector assembly of claim 1 wherein the conductor array is comprised of at least one conductor having a longitudinal body and an end and wherein each said conductor body is split longitudinally at its end.

20. The connector assembly of claim 1 wherein said channel of said nonconducting lead holder is further comprised of a wall for holding said electrical lead array of an implantable electrode.

* * * * *